(12) United States Patent
Bartels

(10) Patent No.: US 8,900,601 B2
(45) Date of Patent: Dec. 2, 2014

(54) PERMEABLE MIXTURES, METHODS AND COMPOSITIONS FOR THE SKIN

(76) Inventor: Jennifer Bartels, Hammond, LA (US)

( * ) Notice: Subject to any disclaimer, the term of this patent is extended or adjusted under 35 U.S.C. 154(b) by 98 days.

(21) Appl. No.: 13/076,877

(22) Filed: Mar. 31, 2011

(65) Prior Publication Data

US 2011/0243856 A1    Oct. 6, 2011

Related U.S. Application Data

(60) Provisional application No. 61/319,398, filed on Mar. 31, 2010.

(51) Int. Cl.
| | | |
|---|---|---|
| A61K 9/00 | (2006.01) | |
| A61K 31/695 | (2006.01) | |
| A61K 45/06 | (2006.01) | |
| A61K 33/24 | (2006.01) | |
| A61K 47/44 | (2006.01) | |
| A61K 33/30 | (2006.01) | |
| A61K 47/06 | (2006.01) | |

(52) U.S. Cl.
CPC .............. *A61K 31/695* (2013.01); *A61K 45/06* (2013.01); *A61K 9/0014* (2013.01); *A61K 33/24* (2013.01); *A61K 47/44* (2013.01); *A61K 33/30* (2013.01); *A61K 47/06* (2013.01)
USPC ........................................................ 424/400

(58) Field of Classification Search
None
See application file for complete search history.

(56) References Cited

U.S. PATENT DOCUMENTS

| | | | |
|---|---|---|---|
| 4,346,709 A | 8/1982 | Schmitt | |
| 4,719,111 A | 1/1988 | Wilson | |
| 4,778,679 A | 10/1988 | Silvetti | |
| 4,847,083 A | 7/1989 | Clark | |
| 4,868,169 A | 9/1989 | O'Laughlin et al. | |
| 4,992,476 A | 2/1991 | Geria | |
| 5,266,318 A * | 11/1993 | Taylor-McCord | 424/744 |
| 5,378,468 A | 1/1995 | Suffis et al. | |
| 5,512,274 A | 4/1996 | Phinney | |
| 5,516,517 A | 5/1996 | Gardner | |
| 5,547,661 A | 8/1996 | Sun et al. | |
| 5,549,887 A | 8/1996 | Galleguillos et al. | |
| 5,632,974 A | 5/1997 | Galleguillos et al. | |
| 5,648,083 A * | 7/1997 | Blieszner et al. | 424/402 |
| 5,672,340 A | 9/1997 | Sun et al. | |
| 5,833,965 A | 11/1998 | Sun et al. | |
| 6,013,271 A | 1/2000 | Doughty et al. | |
| 6,103,245 A | 8/2000 | Clark et al. | |
| 6,121,317 A | 9/2000 | Wu et al. | |
| 6,159,480 A | 12/2000 | Tseng et al. | |
| 6,423,323 B2 | 7/2002 | Neubourg | |
| 6,437,165 B1 | 8/2002 | Mandala et al. | |
| 6,558,695 B2 | 5/2003 | Luo et al. | |
| 6,562,368 B2 | 5/2003 | Hsu et al. | |
| 6,565,879 B1 | 5/2003 | Luo et al. | |
| 6,573,282 B1 | 6/2003 | Yaksh et al. | |
| 6,586,000 B2 | 7/2003 | Luo et al. | |
| 6,602,912 B2 | 8/2003 | Hsu et al. | |
| 6,616,937 B2 * | 9/2003 | Amano | 424/401 |
| 6,632,836 B1 | 10/2003 | Baker et al. | |
| 6,645,520 B2 | 11/2003 | Hsu et al. | |
| 6,649,145 B2 | 11/2003 | McGrath et al. | |
| 6,656,928 B1 | 12/2003 | McCadden | |
| 6,673,363 B2 | 1/2004 | Luo et al. | |
| 6,682,732 B1 | 1/2004 | Blake et al. | |
| 6,706,724 B2 | 3/2004 | Khanapure et al. | |
| 6,719,997 B2 | 4/2004 | Hsu et al. | |
| 6,805,875 B2 | 10/2004 | Bartels | |
| 6,821,523 B2 | 11/2004 | Maibach et al. | |
| 6,825,185 B2 | 11/2004 | Khanapure et al. | |
| 6,835,392 B2 | 12/2004 | Hsu et al. | |
| 6,846,837 B2 | 1/2005 | Maibach et al. | |
| 6,905,675 B2 | 6/2005 | Shacknai et al. | |
| 6,936,627 B2 | 8/2005 | Garvey et al. | |
| 6,943,197 B2 | 9/2005 | Maibach et al. | |
| 7,014,630 B2 | 3/2006 | Rosati et al. | |
| 7,018,464 B2 | 3/2006 | Noguchi | |
| 7,067,553 B2 | 6/2006 | Suh et al. | |
| 7,071,170 B2 | 7/2006 | Kaneko | |
| 7,083,806 B2 | 8/2006 | Rippon et al. | |
| 7,129,251 B2 | 10/2006 | Garvey et al. | |
| 7,256,205 B2 | 8/2007 | Garvey et al. | |
| 7,303,759 B2 | 12/2007 | Mershon | |
| 7,338,670 B2 | 3/2008 | Dewhirst et al. | |
| 7,426,595 B2 | 9/2008 | Osaka | |
| 7,514,432 B2 | 4/2009 | Leblond et al. | |
| 7,540,283 B2 | 6/2009 | Loori et al. | |
| 7,557,087 B2 | 7/2009 | Rothbard et al. | |
| 7,563,224 B2 | 7/2009 | Puchek | |
| 7,625,575 B2 | 12/2009 | Wagoner | |
| 2004/0228811 A1 | 11/2004 | Krzysik | |
| 2006/0078518 A1 * | 4/2006 | Elder et al. | 424/63 |
| 2007/0092468 A1 * | 4/2007 | Brieva et al. | 424/70.7 |
| 2007/0098656 A1 | 5/2007 | Gerrish et al. | |
| 2007/0196325 A1 | 8/2007 | Zhang et al. | |
| 2008/0131381 A1 * | 6/2008 | Chaudhuri et al. | 424/59 |
| 2008/0152678 A1 * | 6/2008 | Shah et al. | 424/401 |
| 2008/0213198 A1 * | 9/2008 | Lintner et al. | 424/59 |
| 2009/0068255 A1 | 3/2009 | Yu et al. | |

FOREIGN PATENT DOCUMENTS

| | | |
|---|---|---|
| WO | WO 2006-026168 A1 | 3/2006 |
| WO | WO2009064412 | 11/2008 |
| WO | WO 2009-100406 A2 | 8/2009 |

OTHER PUBLICATIONS

"Handbook of acid-base indicators", R.W. Sabnis, CRC Press, p. 142, 2008.*
International Search Report of corresponding PCT Application PCT/US2011/030693, mailed Dec. 26, 2011.

* cited by examiner

*Primary Examiner* — Nissa Westerberg
(74) *Attorney, Agent, or Firm* — Todd L. Juneau

(57) ABSTRACT

Topical mixtures with ranges of permeability which promote dermal healing, wound stage arrest, skin cooling, and patient comfort through pH adjustment, therapeutic ingredient carriage, water and oxygen delivery, with superior aesthetics and ease of cleaning features.

5 Claims, No Drawings

PERMEABLE MIXTURES, METHODS AND COMPOSITIONS FOR THE SKIN

CROSS REFERENCE TO RELATED APPLICATIONS

This application claims priority benefit under 35 USC 119(e) to U.S. provisional application Ser. No. 61/319,398, filed 31 Mar. 2009, the contents of which are incorporated herein in their entirety.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

REFERENCE TO A SEQUENCE LISTING

Not applicable.

FIELD OF THE INVENTION

This invention relates to methods and permeable compositions for treating skin conditions while allowing full access to the skin for both oxygen and therapeutic topical drugs.

BACKGROUND OF THE INVENTION

The ability to provide therapeutic topical drugs and/or oxygen to distressed skin tissue in order to promote healing is critical for many medical skin conditions.

Most of the skin or mucosal membrane diseases or disorders are the result of inflammation caused by aging processes, metabolic disorders, surgical and post surgical procedures, environmental and lifestyle conditions, personal hygiene deficiencies, injuries, and inflammatory agents, in which systemic conditions within the body generally yield problematic skin and add to the breakdown and overacidity of the skin, such as, but not limited to, bacterial, fungal, viral, parasitic, autoimmune, allergic, hormonal and/or malignant inflammatory agents. The most common skin diseases or disorders include diabetic skin conditions, pressure ulcers caused by friction and shearing, diaper or infant rashes, incontinence dermatitis and abraded, excoriated skin, eczema, psoriasis and general dermatitis, including contact dermatitis, atopic dermatitis and seborrheic dermatitis. Other common skin injuries include flame, sun, and radiation induced burns, bites from insects and animals, sports chafing and heat rash injuries, and infections from ingrown hairs or nails in the nailbed, along with dry, cracked feet, hands and extremities due to both disease and environmental factors.

In the Textbook of Aging Skin, 2008, Miranda Farage, Kenneth W. Miller, and Howard J. Maibach, incorporated herein by reference in its entirety, it is noted: "Although the human skin is incredibly durable, like all other organ systems, it is affected by aging. A sophisticated and dynamic organ comprising 17% of the body's weight, the skin primarily acts as the barrier between the internal environment and the world outside. Yet it performs numerous functions beyond simply acting as a barrier: homeostatic regulation, prevention of percutaneous loss of fluid, electrolytes, and proteins, temperature maintenance; sensory perception; and immune surveillance.

"Distinguishing the precludable aspects of cutaneous aging (primarily hormonal and lifestyle influences) from the inexorable (primarily intrinsic aging) is essential to preventing and treating the ailments of the aging skin."

Aging processes and inactivity, combined with diabetic conditions in long term care settings pose some of the most advanced dermatological problems, affecting the patient's health as a whole.

In the Textbook of Aging Skin, 2008, Miranda Farage, Kenneth W. Miller, and Howard J. Maibach, it is noted: "Because permeability (of the skin itself) does not appear to be significantly increased in the skin of the aged individual, it has been generally assumed that barrier function does not alter significantly with aging." Thus, while skin itself becomes increasingly distressed and/or compromised due to the aging process, the importance of the barrier function played by skin does not change as we age.

In pressure wound staging, wounds can be classified from Stage I to IV with the addition of an unstageable wound as follows:

Stage I is the most superficial, indicated by non-blanchable redness that does not subside after pressure is relieved. This stage is visually similar to reactive hyperemia seen in skin after prolonged application of pressure. Stage I pressure ulcers can be distinguished from reactive hyperemia in two ways: a) reactive hyperemia resolves itself within $\frac{3}{4}$ of the time pressure was applied, and b) reactive hyperemia blanches when pressure is applied, whereas a Stage I pressure ulcer does not. The skin may be hotter or cooler than normal, have an odd texture, or perhaps be painful to the patient. Although easy to identify on a light-skinned patient, ulcers on darker-skinned individuals may show up as shades of purple or blue in comparison to lighter skin tones.

Stage II is damage to the epidermis extending into, but no deeper than, the dermis. In this stage, the ulcer may be referred to as a blister or abrasion.

Stage III involves the full thickness of the skin and may extend into the subcutaneous tissue layer. This layer has a relatively poor blood supply and can be difficult to heal. At this stage, there may be undermining damage that makes the wound much larger than it may seem on the surface Stage IV is the deepest, extending into the muscle, tendon or even bone.

Unstageable pressure ulcers are covered with dead cells, or eschar and wound exudate, so the depth cannot be determined.

Research has indicated that most pressure ulcers are acidic in the most inflamed areas, and that aging skin becomes more acidic over time. According to the Archives of Dermatological Research, volume 298, number 9, 413-420, incorporated by reference herein in its entirety, wound healing is a complex regeneration process, which is characterized by intercalating degradation and reassembly of connective tissue and epidermal layer. The pH value within the wound-milieu influences indirectly and directly all biochemical reactions taking place in this process of healing. Interestingly, pH is so far a neglected parameter for the overall outcome. For more than three decades the common assumption amongst physicians was that of a low pH value, such as it is found on normal skin, is favorable for wound healing. However, investigations have shown that in fact, some healing processes such as the take-rate of skin grafts require an alkaline environment.

If pH adjustment is to be done, then the methods of delivery of that pH adjustment must be optimally brought together for maximum efficiency. Adjustment of wound pH using varying methods has been done for years using very slow, expensive, inaccessible means such as sugar mixtures and betadyne. Such hand-compounded methods are replete with opportunities for infection to occur, inconsistencies in batch production, and by no stability testing yielding unreliable shelf life data. In the past, anecdotal evidence led the wound care community down different paths in their search for optimum wound care and healing methods and compositions. It is also known that there is a key factor in hospital efficiency and better patient care for a Stage II wound not to be allowed to progress to a Stage III, resulting in that patient being able to be discharged from the facility. An added benefit of stopping a Stage II from becoming a Stage III wound is overall patient care cost reduction in the facility.

Dermatitis and other injury to the skin occurs when the skin is subjected to biological processes, environmental and lifestyle conditions, and/or conditions that breakdown the stratum corneum. The stratum corneum (SC), or outermost layer of the epidermis, consists of corneocytes embedded in lipid multilayers and serves as the main barrier for skin penetration of various topical drugs. The main purpose of this part of the skin is to reduce water loss, repel microbial infection, protect deeper layers, and provide a water-repellant layer. Damage to this layer can occur, for example, when an infant's skin is exposed for long periods to urine and feces, these waste products lower the skin pH and result in the breakdown of the stratum corneum, which is thinner in infants compared to adults. Although moisture alone will loosen this layer and allow for friction irritation to occur, urine breakdown by fecal enzymes can reduce, or acidify, the skin resulting in chemical irritation. Decubitus ulcers can occur when patients must spend long periods in bed, and the resulting pressure points on the skin cause irritation lesions, commonly called bedsores. Some studies have shown that 8-40% of intensive care patients suffer from decubitus ulcers. According to a 2004 study, the incidence rate for decubitus ulcers calculated 474,692 new cases per year, with 34,320 deaths resulting therefrom. Another study calculated that 8% of spinal cord patients died as a result of decubitus ulcers and their complications.

The anatomical localization of the main barrier against diffusional water loss through the skin has often been considered to be the horny layer. The relative importance of the different layers of the SC has long been discussed. Some consider the horny layer uniform in functional barrier characteristics, whereas others consider it nonidentical. Based on lipid analysis and barrier properties, it has been suggested that the lowest region of the horny layer is mainly responsible for preventing evaporative water loss. Previous studies have also shown that transepidermal water loss (TEWL) increases while SC pH value decreases with decreasing thickness of the horny layer. See, Assessment of Stratum Corneum Bartier Layer and pH Changes by Means of Tape Stripping, Tam Tiet, et al., JAAD, March 2005, incorporated by reference herein in its entirety.

The wound healing process, depending on the type of injury to the skin, is an intricate process that involves the steps of inflammation, proliferation, and remodeling. During inflammation, bacteria and debris are phagocytized and removed, and factors are released that cause the migration and division of cells involved in the proliferative phase.

The proliferative phase is characterized by angiogenesis, deposition of collagen, formation of granular tissue, re-epithelialization, and wound contraction. In angiogenesis, new blood vessels are formed by vascular endothelial cells. In fibroplasia and formation of granular tissue, fibroblasts grow and form a new, provisional extracellular matrix (ECM) by excreting collagen and fibronectin.

Simultaneously, re-epithelialization occurs, providing a new epithelial layer. It is at this stage that oxygenation of the skin is critical to wound healing.

In the remodeling phase, collagen is remodeled and realigned along tension lines and cells that are no longer needed are removed by apoptosis.

Animal studies have shown that several of the processes of skin healing and repair are affected by the subcutaneous partial pressure of oxygen ($O_2$). For example, supplemental oxygen can lead to increased rate of collagen deposition, epithelialization and improved healing of split thickness grafts. Increased subcutaneous $O_2$ has also been shown to improve bacterial defenses.

As is evident from the above descriptions, one of the important routes of administration of a drug for treating a skin or mucosal membrane is by topical application of a drug onto the skin or mucosal membrane. Such drugs can include antibiotics, antifungals, antivirals, anti-inflammatories, pH adjusters and analgesics.

Common treatments include use of zinc oxide pastes, powders, petroleum-based creams, and even mild steroid creams to reduce excess moisture, provide antibacterial activity or barriers, and to reduce damage caused by the body's own inflammatory processes. Similar treatments are used in hospital settings to treat adult patient decubitus ulcers.

Many products in the topical pharmaceutical market have been geared towards occlusive mixtures. These occlusive mixtures can be beneficial to distressed skin in that they tend to be effective in protecting skin from the elements, moisture, and other irritants such as excrement or secretions. Unfortunately, in the same way that occlusive topical compositions block skin access to harmful irritants, they simultaneously block skin access to oxygen and other agents that promote healing.

Occlusive topical compositions also tend to yield a thick, greasy consistency. These are often called barrier creams and ointments, and generally, they are petrolatum or zinc oxide based. Compositions of this nature can be difficult to spread thinly and evenly. Such compositions can also be difficult to clean without subjecting the underlying skin to friction that is likely to cause or worsen irritation or inflammation.

While describing the problems associated with occlusive compositions, U.S. Pat. No. 7,682,623 to Eini, discloses a pharmaceutical or cosmetic carrier or composition for topical application characterized by rheological properties which render the carrier or composition semi-solid at rest and a liquid upon application of shear forces thereto. The referenced patent relates that both pharmaceutical agents and ambient oxygen are impeded by an ointment or barrier with a petroleum (petrolatum) base. "The active drug ingredient, which is dissolved or dispersed in the petroleum carrier, is not efficiently absorbed into the wound tissue, thus the efficacy of the drug is affected." Further, the patent states that " . . . petroleum (petrolatum) restricts respiration of a wound tissue and is disturbing to the normal respiration of the skin."

In addition, U.S. Pat. No. 6,013,271, to Doughty, et al., discloses a skin care composition in the form of an oil-in-water dispersion which comprises from about 1% to about 60% oil phase components. In detailing the benefits of water-based topical compositions over petroleum-based, the referenced patent states that a water-based composition "provides skin care cosmetic compositions which provide improvements in moisturizing, absorption, skin feel, skin care, and appearance characteristics and which in particular provide improved short and longer term moisturizing effectiveness, while at the same time reducing stickiness and avoiding a greasy feel on the skin. The compositions also display excellent stability characteristics at both normal and elevated temperatures."

In addition, U.S. patent application Ser. No. 12/700,375 to Bartels, discloses methods and compositions for treating wounds, decubitus ulcers, diaper rash, burns, abrasions, and other irritations and relevant injuries, including, in one embodiment, the use of an aqueous or emollient medium having one or more pH raising ingredients in a composition specifically designed to deliver oxygen to the skin's surface.

The problem of the drawbacks, discomfort, and potential infection risk that occlusive mixtures pose would be addressed by the introduction of an acceptable nonocclusive composition and method of topical application. To address the issue in the field of over the counter topical medications, such nonocclusive composition must also comply with FDA labeling requirements for over the counter topical solutions.

Accordingly, there is still a need for nonocclusive topical compositions and methods of treatment for damaged or irritated skin that both protect the skin surface, assist in its barrier and water-retention functions while allowing the simultaneous delivery of therapeutic agents and oxygen to the skin in a convenient and efficient manner.

BRIEF SUMMARY OF THE INVENTION

Topical compositions permeable to most chemical compounds can act as effective carriers of both active and nonactive ingredients in a mixture. Such compositions can provide soothing water or gel-based moisture to the skin, while also utilizing the permeability of such compositions to provide oxygen with access to the treated skin.

The invention contemplates in one embodiment the use of a water-based or gel-based topical composition specifically designed to allow the delivery of both therapeutic active and nonactive ingredients, as well as oxygen, to the skin's surface in order to promote healing.

In one preferred embodiment, there is provided a dermatological composition, comprising water or gel mixtures 50%-99% wt.; petrolatum 0-50% wt.; one or more of zinc oxide or titanium oxide 0-20% wt.; and dimethicone 0%-30% wt.; and wherein weight % is based on the total weight of the composition and the weight percentages of all components in the composition totals 100%.

In another preferred embodiment, there is provided the dermatological composition, further comprising one or more pH raising, mediating or adjusting ingredients, totaling 0.1%-20% wt.

In another preferred embodiment, there is provided the dermatological composition, further comprising one or more natural therapeutic ingredients, totaling 0%-15% wt.

In another preferred embodiment, there is provided the dermatological composition, further comprising one or more antibacterial or antiseptic ingredients, totaling 0%-10% wt.

In another preferred embodiment, there is provided the dermatological composition, further comprising one or more thickening agents, totaling 0%-25% wt.

In another preferred embodiment, there is provided the dermatological composition, further comprising one or more emulsifiers, totaling 0.1-20% wt.

In another preferred embodiment, there is provided the dermatological composition, further comprising one or more preservatives, totaling 0.1%-15% wt.

In another preferred embodiment, there is provided the dermatological composition, optionally further comprising one or more humectants, totaling 0.1%-10% wt.

In another preferred embodiment, there is provided a dermatological composition, comprising water or gel mixtures 40%-80% wt.; petrolatum 0-50% wt.; oils from the group containing mineral oil, coconut oil, sweet almond oil, vegetable oil or other dermatologically acceptable substitutes 0%-60% wt.; aloe 1-60%; one or more zinc oxide or titanium dioxide 0-20% wt.; dimethicone 0%-30% wt.; one or more pH raising, mediating or adjusting ingredients 0.1%-20% wt.; one or more natural therapeutic ingredients 0%-15% wt.; one or more antibacterial or antiseptic ingredients 0%-10% wt.; one or more thickening agents, totaling 0%-25% wt.; one or more emulsifiers 0.01-20% wt.; one or more pharmaceutically acceptable preservatives 0.1%-15% wt., and one or more humectants, totaling 0%-10% wt; further comprising wherein the dermatological composition is in the form of a cream or an ointment, and wherein weight % is based on the total weight of the composition and the weight percentages of all components in the composition totals 100%.

In another preferred embodiment, there is provided a dermatological composition, comprising water or gel mixtures 40%-90% wt.; petrolatum 0-41% wt.; oils from the group containing mineral oil, coconut oil, sweet almond oil, vegetable oil or other dermatologically acceptable substitutes 0%-50% wt.; one or more zinc oxide or titanium oxide 0-16% wt.; dimethicone 0.5%-10% wt.; one or more pH raising ingredients 0.1%-15% wt.; one or more natural therapeutic ingredients, 0%-10% wt.; one or more antibacterial or antiseptic ingredients 0.1%-25% wt.; one or more emulsifiers 0.08-17% wt.; one or more preservatives, 0.1%-10% wt.; and one or more humectants, 0.1%-5% wt; and wherein weight % is based on the total weight of the composition and the weight percentages of all components in the composition totals 100%.

In another preferred embodiment, there is provided a dermatological composition, comprising water or gel mixtures 50-75% wt.; petrolatum approximately 15% wt.; mineral oil approximately 8% wt.; ceresin wax approximately 5% wt.; dimethicone approximately 1% wt.; lanolin alcohol approximately 7% wt.; aluminum hydroxide approximately 0.75% wt.; magnesium hydroxide approximately 0.68% wt.; sorbitan sesquioleate less than 5% wt.; sorbitol less than 3% wt.; and preservatives less than 1% wt.

In another preferred embodiment, there is provided the composition according to any of paragraphs 40, 48, 49 or 50, in the form of an ointment, lotion, cream, emulsion, suspension, ointment, gel, bath, soak, spray, powder, or foam.

In another preferred embodiment, there is provided the composition according to any of paragraphs 40, 48, 49 or 50, in the form of a cream or an ointment.

In another preferred embodiment, there is provided the composition according to any of paragraphs 40, 48, 49 or 50, in a delivery vehicle selected from a single use, individualized, sterile packets, a pre-soaked wrap, bandage or dressing, a pre-soaked undergarment, a pre-soaked wipe, treated applicator, an infused film for application to the skin, or an infused sponge with applicator stick for use in oral care to treat mouth sores.

In another preferred embodiment, there is provided the composition according to any of paragraphs 40, 48, 49 or 50, in combination with an additional therapeutic agent.

In another preferred embodiment, there is provided the composition according to any of paragraphs 40, 48, 49 or 50, in combination with one or more nonocclusive cleansing agents.

In another preferred embodiment, there is provided the composition according to any of paragraphs 40, 48, 49 or 50, further comprising 0.1%-10% wt. of a litmus dye or other pharmaceutically acceptable acid-base indicator.

In another preferred embodiment, there is provided a method for delivering therapeutic dermatological agents to skin while maintaining access to the treated skin surfaces by other therapeutic agents, comprising the step of topically applying a dermatologically acceptable permeable composition according to any of paragraphs 40, 48, 49 or 50.

In another preferred embodiment, there is provided a method for treating a skin condition, comprising the step of topically applying a dermatologically acceptable composition according to paragraphs 40, 48, 49 or 50 to a patient having said skin condition.

In another preferred embodiment, there is provided a method of counteracting pain, itching or other discomfort in human skin, comprising the step of topically applying a dermatologically acceptable composition as in any of paragraphs 40, 48, 49 or 50 to a patient.

In another preferred embodiment, there is provided a method of creating a cooling sensation in human skin, comprising the step of topically applying a dermatologically acceptable composition as in any of paragraphs 41, 48, 49 or 50 to a patient.

In another preferred embodiment, there is provided a method of raising, mediating or adjusting the pH of human skin by topically applying a dermatologically acceptable composition as in any of paragraphs 41, 48, 49 or 50 to a patient, wherein the skin to which the composition is so applied has a lowered pH due to a wound or other traumatic condition.

In another preferred embodiment, there is provided a method of delivering oxygen to human skin, with or without pH adjustment, by topically applying a dermatologically acceptable composition as in any of paragraphs 40, 48, 49 or 50 to a patient.

In another preferred embodiment, there is provided a method of treating symptoms of diabetes, including without limitation the skin of a diabetic patient's feet, by topically applying a dermatologically acceptable composition as in any of paragraphs 40, 48, 49 or 50 to a patient.

In another preferred embodiment, there is provided a method of treating eczema by topically applying a dermatologically acceptable composition as in any of paragraphs 40, 48, 49 or 50 to a patient.

In another preferred embodiment, there is provided a method of treating skin surrounding an -ostomy or PEG site by topically applying a dermatologically acceptable composition as in any of claims paragraphs 40, 48, 49 or 50 to a patient.

In another preferred embodiment, there is provided a method of treating skin susceptible to irritation associated with friction related to the removal of topical compositions by topically applying a dermatologically acceptable composition as in any of claims paragraphs 40, 48, 49 or 50 to a patient.

In another preferred embodiment, there is provided a method of determining the approximate pH of a treated area by topically applying a dermatologically acceptable composition as in paragraph 56, by observing the presence or absence of a color shift in the composition upon application.

In another preferred embodiment, there is provided a method of mitigating or halting pressure wound stage progression by topically applying a dermatologically acceptable composition as in any of paragraphs 40, 48, 49 or 50 to a patient.

DETAILED DESCRIPTION OF THE INVENTION

Topical pharmaceutical compositions and methods, wherein such compositions are permeable to oxygen, water and other therapeutic compounds, whether internal or external to the composition.

Herein, the term "Darcy" means a unit of measurement equivalent to the passage of one cubic centimeter of fluid (having a viscosity of one centipoise) per second through a sample one square centimeter in cross-sectional area under a pressure of one atmosphere per centimeter of thickness.

Herein, the term "Darcy's Law" means a simple proportional relationship between the instantaneous discharge rate through a porous medium, the viscosity of the fluid and the pressure drop over a given distance.

Herein, the terms "permeable" or "nonocclusive" are used interchangeably to describe a material or composition that allows liquids or gases to pass through it.

Herein, the term "poise" (symbol P) means the unit of dynamic viscosity in the centimeter gram second system of units.

The range of mixtures described herein presents a sophisticated and finely tuned composition that is permeable so as to allow delivery of oxygen or therapeutic agents in a viscous state so as to be breathable but also to cling to the skin. The composition will also deliver water moisture to the skin, with or without the presence of occlusive, semiocclusive, or nonocclusive wound dressings.

In a preferred embodiment the composition is an ointment or cream, comprising an oil-in-water emulsion containing both active and inactive ingredients to treat a skin condition, while also allowing oxygen and other therapeutic agents to permeate the composition and reach the skin.

In a preferred embodiment, the composition base contains a range of at least 40% water and/or nonocclusive humectants. These hydrophilic base components may act as carriers for other therapeutic agents.

In another preferred embodiment, the composition may also utilize water and/or nonocclusive humectants as emollients, allowing the composition to absorb into the stratum corneum and treat the skin from within. The ease of absorption into the skin of a water or gel-based composition yields multiple therapeutic benefits to damaged or irritated skin.

In addition to effecting greater therapeutic delivery capability as compared to petroleum-based products, a water or gel-based composition also requires little or no active clean up in removal due to its more fluid consistency and the fact that a substantial percentage of the composition is absorbed into the skin. The fact that such composition requires little or no cleanup means that no cleanup-related friction need be applied to the skin as it heals.

Emollients, therapeutic mixtures, skin protectants, topical analgesics, anti-itch medications, antiseptic mixtures, antibacterial products and soaked dressings, wipes or other devices contemplated herein include natural and manmade materials, including mineral oil 5-30% wt., petrolatum 3-20% wt., zinc oxide 1-16%, titanium dioxide 1-7%, sorbitol 0-20% wt. including specifically the range of 3-10% wt., sortiban 0-20% wt. including specifically the range of 3-10% wt., dimethicone 0-7% wt. including 1-3% wt., cyclomethicone 1-3% wt., isopropyl myristate 0.1-10% wt., lactic acid 0.1-10% wt., aloe 1-50%, sodium lactate 0.1-5% wt., sodium hyaluronate 0.25-2% wt., and glycerin.

Emulsifiers contemplated herein include sorbitan sesquioleate 0-15% wt., polysorbate 20, propylene glycol, carbomer incl. carbomer 940, emulsifying wax NF, beeswax, ceresin, microcrystalline wax, waxes used in cosmetics, glyceryl monostearate, starch, palm stearic acid, trienthanolamine, and xanthan gum.

Additional binders, stabilizers, preservatives, colorants, and fragrances, known to a person of ordinary skill in the art, are contemplated as within the scope of this invention. Some preferred additional ingredients include, as examples without being limited thereto, lanolin alcohol 0-15% wt. including 1-3% wt., phenoxyethanol 0-5% wt. including 0.1%-1.0% wt., ethylhexylglycerin 0-5% including specifically the range of 0.1%-1.0% wt., and BHT 0.1%-1.0% wt.

In a preferred embodiment as an ointment, the medium is comprised of one or more pH raising, mediating or adjusting components selected from sodium bicarbonate, calcium carbonate, magnesium hydroxide, aluminum hydroxide, sodium hydroxide, and/or cesium chloride. Additional pH adjusters contemplated herein include lactic acid, citric acid and acetic acid.

In a preferred embodiment, the pH of the composition ranges from about 6.8 to about 10.4, and more preferably from about 8.8 to about 9.5. In another preferred embodiment, the pH of the composition ranges from about pH 8.2 to about pH 9.3.

Litmus dye, a purple liquid extracted from lichens, is used in tests determining the pH of substances, usually being soaked in litmus paper. The dye is purple, and therefore contains components that reflect both red and blue light. Litmus paper comes in blue and red shades. When the blue litmus paper turns red, an acid has donated hydrogen ions to the substance, allowing it to absorb more blue light and reflect more red. When the red litmus paper turns blue, the opposite reaction occurs, indicating the presence of a base.

When in contact with a base, the blue paper remains blue and when in contact with an acid, the red paper remains red. In such a case, the same portion of the light spectrum is already being absorbed, so nothing changes. Also, when the litmus paper comes in touch with water or other neutral or nearly-neutral substances, there is no change, because a neutral substance neither donates nor removes ions from the paper.

In addition to litmus dye, other common acid-base indicators include, without limitation, methyl violet, thymol blue, methyl yellow, methyl, bromcresol green, methyl red, bromthymol blue, and phenolphthanlein.

In another preferred embodiment, the composition would include 0.1%-10% wt. of a litmus dye or other pharmaceutically acceptable acid-base indicator to determine the approximate pH of a treated area by the presence or absence of a color shift in the composition upon application.

Although not to be limited by a particular theory, it is believed that an alkaline environment and alkaline chemistry in an already highly permeable mixture can act to enhance further the level of oxygen that is provided to the tissues to facilitate healing of a wound.

The ointments, creams, and salves contemplated herein may be an oil-in-water emulsion, with droplets of nonpolar liquid suspended in a polar medium, or a water-in-oil emulsion, with droplets of polar liquid suspended in a nonpolar medium. The oil phase ingredients are mixed. Heat may be required of wax-blends. The water phase ingredients are also mixed. Processing for an oil-in-water emulsion starts with blending at high speed the water phase and the oil phase is added slowly to allow the emulsion to form. Processing for a water-in-oil emulsion is accomplished by adding the water phase to the oil phase during high speed blending to allow the emulsion to form.

The polarity of the medium of an emulsion determines which substances will blend well with that emulsion. Since oil-in-water emulsions will mix readily with other polar, water-based liquids, while water-in-oil emulsions mix more easily with nonpolar oils, the type of emulsion used will be determined based on the type(s) of therapeutic agents being delivered through a given embodiment of the composition.

To facilitate understanding of the invention set forth in the disclosure that follows, a number of terms are defined herein.

The term "wound" used herein refers broadly to injuries to the skin and subcutaneous tissue initiated in any one of a variety of ways (e.g., pressure sores from extended bed rest, wounds induced by trauma, cuts, ulcers, burns and the like) and with varying characteristics. Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that exhibits impaired healing parameters interfering with the physiological sequence of events. These wounds tend to prolong and/or halt healing time course, subjecting the wounds to further complications such as recurrent infections and necrosis.

The present invention contemplates treating all skin wound types and of all grades, including deep wounds and chronic wounds, as well as skin damage.

The term "skin wound" refers to any type of epithelial wound including, but not limited to, an ulcer such as a diabetic ulcer, a pressure ulcer, a diabetes-related wound, a burn, a sun burn, an aging skin wound, an inflammatory disease wound, a skin blistering wound, a psoriasis wound, a diabetic wound, a laceration, a surgical incision wound, and a post surgical adhesions wound.

The term "skin damage" as used herein refers to any type of skin damage or condition such as, for example, inflammation, irritation, abrasions, cuts, burns, rashes, scrapes, wounds, auto-immune related damage, infection related damage, and other types of breakdown of the stratum corneum, epidermis, and underlying tissues.

The term "epidermis" refers to the outer most layer of the skin.

Dermatological compositions of the invention may be utilized for treatment of a wide variety of dermal conditions and adverse physiological states manifesting dermally, including, without limitation, incontinence dermatitis, decubitus skin ulcers, dry skin/xerosis, psoriasis, ichthoyosis, keratosis, keratoderma, dermatitis including but not limited to pediatric diaper dermatitis, geriatric bedsores, seborrheic dermatitis, contact dermatitis, chemical injury, burns from heat, chemicals, electricity, sunlight or radiation, itching, pruritis, eczema, callouses, and burn wounds.

The term "healing" in respect to a wound or a skin damage refers to a process to repair a wound, or to repair the skin damage.

The phrase "inducing or accelerating a healing process of a skin wound or skin damage" refers to either the induction of the formation of granulation tissue of wound contraction and/or the induction of repithelialization (i.e., the generation of new cells in the epithelium). Wound healing is conveniently measured by decreasing wound area.

As used herein, the phrase "pharmaceutical composition" refers to a preparation of one or more of the active ingredients described herein with other chemical components such as physiologically suitable carriers and excipients. The purpose of a pharmaceutical composition is to facilitate administration of a composition to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of an administered active ingredient. An adjuvant is included under these phrases.

The term "excipient" as used herein refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The various compositions of the invention may be in the form of lotions, creams, emulsions, suspensions, ointments, gels, baths, soaks, sprays, infused dressing, powder, foam, or other suitable forms capable of administration to the skin of a user. Accordingly, compositions in which water and/or water-miscible solvents are employed in varying amounts, are contemplated. Additionally, the compositions may be formulated with adjuvants, additional active ingredients and/or excipients, and/or other ingredients, to impart specific thixotropy, viscosity, flow, spreading, self-leveling, or other characteristics thereto, as necessary or desirable in specific formulations.

The term "cream" refers to a topical medication form that is a water-based emulsion.

The term "ointment" refers a topical medication form that is an oil-based emulsion.

The term "lotion" refers to a topical medication form that is low to medium viscosity emulsion, including an oil-in-water emulsion or a water-in-oil emulsion.

The term "gel" refers to a topical medication form that liquifies upon contact with skin, and specifically includes, without limitation, hydrogels.

Hydrogels are water-based products used to maintain a moist wound-healing environment, with proven effectiveness in the art.

The term "paste" refers to a topical medication form that is a combination of oil, water, and a powder, i.e an ointment in which the powder is suspended.

Compositions of the invention are usefully employed as skin moisturizers, skin softening agents, skin debridement agents, etc., as well as base composition for cosmetic formulations, as well as base compositions for therapeutic, e.g., pharmacological, formulations. In cosmetic formulations, the compositions of the invention may be used with added ingredients that are solely cosmetic. Alternatively, the cosmetic formulation may include ingredients that are both cosmetically efficacious and therapeutically effective, e.g., so-called "cosmeceutical" ingredients.

In therapeutic formulations, the compositions of the invention may be utilized as base compositions for topical administration of therapeutic agents such as wound healing agents, anti-inflammatory agents, e.g., non-steroidal anti-inflammatory agents, glucocorticosteroids (e.g., hydrocortisone, triamcinolone, betamethasone, or their respective derivatives, or ibuprofen, ketoprofen, methyl salicylate, etc.), anti-infective (antibiotic) agents (e.g., bacitracin, polymixin B, mupirocin, neomycin, and mixtures thereof), enzymes, anti-fungal agents, anti-viral agents, acne-combating agents, rosacea-combating agents, dermatitis-combating agents, topical immunomodulator agents, etc., as well as any other agents that are beneficially applied to the skin to treat or ameliorate symptoms of physiological disorders and disease states susceptible to such treatment or amelioration, such as for example, zinc oxide.

Set out below is a tabulation of secondary therapeutic agents by category and specific examples, without limitation, for which dermatological compositions of the invention may be utilized in therapeutic formulations. In the use of such therapeutic agents, the composition of the invention as variously described herein, comprising humectant, emollients and optional additional excipients, is utilized as a base to which the therapeutic agent is added in a therapeutically effective amount to yield a corresponding therapeutic composition for combating the appertaining disease state or adverse physiological condition constituting the specific indication.

Analgesics

Lanocaine, lidocaine, prilocalne, salicylates, NSAIDs, acetaminophen, capsaicins, camphor, menthol, methyl salicylate, methyl nicotinate, ketamine and trolamine salicylate.

Wound Healing

Papain, trypsin, allantoin, chymo-trypsin, streptokinase, streptodornase, ficin, pepsin, carboxypeptidase, amino-peptidase, chymopapain, bromelin.

Anti-Inflammatory

Hydrocortisone, triamcinolone, betametamethasone, ibupropfen, ketoprofen, methyl salicylate, dexamethasone, prednisolone, cortisone, prednisone, beclomethasone, betamethasone, flunisolide, fluocinolone acetonide, fluocinonide, indomethacin, diclofenac sodium, mefenamic acid, azulene, phenacetin, isopropylantipyrine, acetaminophen, bendzac, phenylbutazone, flufenamic acid, sodium salicylate, salicylamide, sasapyrine, etodolac.

Anti-Infectives

Bacitracin, polymixin B, mupirocin, neomycin, tetracyclines (chlortetracycline hydrochloride, oxytetracycline hydrochloride and tetracycline hydrochoride), clindamycin, gentamicin sulfate, benzalkonium chloride, benzethonium chloride, hexylresorcinol, methylbenzethonium chloride, phenol.

Antiseptics

Thymol, Menthol, Benzalkonium Chloride, Chlorhexidine gluconate, and natural oils including Tea Tree Oil.

Astringents and Drying Agents

Calamine, witch hazel, sodium bicarbonate, aluminum hydroxide and zinc oxide.

Anti-Fungals

Miconazole, econazole, tolnaftate, ketoconazole, undecylenic acid, amphotericin, carbol-fuchsin, ciclopirox, clotrimazole, haloprogin, mafenide, naftifine, nystatin, oxiconazole, silver, sulfadiazine, sulconazole, terbinafine, tioconazole, undecylenic acid Anti-Acne salicylic acid, benzoyl peroxide, Acne, rosacea, seborheic resorcinol, sulfur, dermatitis sodium sulfacetamide, retinoic acid, isotretinoin, erythromycin, zinc, retinol, citric acid, and alpha hydroxy acid.

Anti-Virals

Acyclovir, docosanol, pencyclovir, cidofovir, desciclovir, famciclovir, ganciclovir, lobucavir, PMEA, valacyclovir, 2242, PAA, PFA, H2G, sorivudine, trifluridin, tromantadine, adenine, arabinoside, arabinosyladenine-monophosphate, lobucavir.

Immunomodulators

Pimecrolimus, tacrolimus, muramyl dipeptide, cyclosporins, interferons (including alpha, beta, and gamma interferons), interleukin-2, cytokines, tumor necrosis factor, pentostatin, thymopentin, transforming factor beta2, erythropoetin.

Cleansers

Ammonium lauryl sulfate, cold creams, glycerin, glycolic or salicylic acid, sodium bicarbonate, calcium carbonate, magnesium hydroxide, aluminum hydroxide, sodium hydroxide, polyethylene beads, aluminum oxide, syndet cleansers, bicarbonate of soda, waxes and minerals with borax-based detergents.

As used herein, references to compositional ingredients in percents by weight refers to weight percentages based on the total weight of the composition or formulation.

It is further proposed that the compositions described herein assist healing in the conventional wound care setting by functioning in its own environment and assisting conventional wound care agents, whatever their delivery forms or state of occlusivity, in doing their intended work towards healing a wound.

Compositions utilizing a water or hydrogel base, given the high permeability of the base and its ease of absorption into the skin, are believed to act as superior carriers for active and inactive therapeutic ingredients, with the added advantage of easy removal for cleaning. Such hydrophilic compositions are thought to improve further upon compositions based instead on hydrophobic compositions based on mineral oils, silicone oils or plant-derived oils, as are widely used in the art.

The Greek physician Galen of Pergamum in the second century AD noted empirically that wounds heal optimally in a moist environment. Nevertheless, for nearly 2000 years, therapeutic efforts focused on drying the wound site, with absorptive gauzes a mainstay of wound management. It was not until the 1960s that Winter proved the critical role of moisture in healing when he demonstrated that acute wounds covered with moisture-retentive occlusive dressings healed twice as rapidly as similar wounds left exposed to air.

See also, Fonder and Lazarus, JAMA Dermatology, February 2008 "Treating the Chronic Wound: A Practical Approach to The Care of Nonhealing Wounds and Wound Care Dressings", incorporated herein by reference in its entirety. An additional benefit water or gel based carriers over occlusive mixtures is the provision of a moisture layer, encouraging water vapor transfer, which encourages wound healing.

The compositions of the present invention are intended to deliver moisture in an innovative way that is independent of the method used to treat any particular patient's wound.

The permeability, with concomitant ease of delivery of active ingredients, oxygen and moisture to the skin, in combination with the pH-raising ingredient(s) described herein, will allow free movement of oxygen, water and other ingredients to and from the skin's surface.

Darcy's Law describes the average behavior of a mixture of a porous medium and one or more fluids. Darcy's Law describes the kinetics of fluid flow through porous media in terms of the driving force and the permeability of the medium. Darcy's Law is given by the equation:

$$Q = \frac{K}{\eta} \frac{\Delta P}{\Delta L} A$$

Q=flow rate in $m^3/s$
K=permeability coefficient ($m^2$)
$\Delta P$=pressure drop or difference (Pa)
L=flow length (m)
A=area of cross-sectional area to flow ($m^2$)
$\eta$=fluid viscosity (Pa-s).

It is contemplated that the present inventive compositions will have an average pore size of the applied compositional matrix to facilitate the flow of water and carbon dioxide, which are approximately 0.320 nm (0.000323 μm) in diameter, as both molecules and aggregates of molecules, while providing a partial barrier to bacteria which can be about 200-2000 nm (0.200 to 2.00 μm) and larger.

The average target pore size for the compositions herein is less than 0.20 μm, but ranges from 0.001 μm-1.00 μm. The average target thickness, or flow length, ranges from about 100 μm to about 1000 μm, preferably from about 120 μm to about 500 μm. Accordingly, permeability coefficients ranging from about 0.00001 μm2 to about 0.001 μm2 are within the scope of the inventive subject matter.

It is contemplated that persons of ordinary skill in the field are able to apply permeability concepts and calculations derived from the unrelated scientific endeavors of petroleum engineering, coatings, and polymers, to the field herein, permeable dermatological compositions for wound healing with the teachings provided herein.

The compositions of the present invention may be packaged in both large and smaller volume containers. In one embodiment, the composition is provided in single use, individualized, sterile packets. In another embodiment, the composition is provided in a pre-soaked bandage or dressing, an undergarment treatment esp. for incontinence dermatitis, a pre-soaked wipe, or an infused film for application to the skin. In another embodiment, the composition is provided in an infused sponge with applicator stick, esp. for use in oral care to treat mouth sores.

EXAMPLES OF COMPOSITIONS

Example 1

Permeable Mixture 1

Water (Aqua) 30-100% wt., Mineral Oil 10-30% wt., Petrolatum 3-30% wt., Sorbitol 3-10% wt., Ceresine Wax 3-17% wt., Sorbitan Sesquioleate 3-10% wt., Lanolin Alcohol 1-15% wt., Dimethicone 1-30% wt., Magnesium Hydroxide 1-10%, Phenoxyethanol<1%, Ethylhexylglycerin<1%, BHT<1%, with optional inclusion of fragrance, coloring, color change agent and/or pH buffer.

Example 2

Permeable Mixture 2

Water (Aqua) 30-85% wt., Mineral Oil 0-10% wt., Petrolatum 10-41% wt., Sorbitol 3-10% wt., Ceresine Wax 3-15% wt., Sorbitan Sesquioleate 3-10% wt., Lanolin Alcohol 5-15% wt., Dimethicone 1-30% wt., Aluminum Hydroxide 1-10% wt., Magnesium Hydroxide 1-10%, Preservatives<1% wt., with optional inclusion of fragrance, coloring, color change agent and/or pH buffer.

ACTUAL EXAMPLES OF TREATMENT

Example 3

Incontinence Dermatitis

An 80 year old woman presenting with extremely red excoriated buttocks due to long term incontinence had been treated with various traditional creams and ointments without success. Ointment of the present invention was topically applied. Within three days of continuous treatment, the skin condition improved.

Example 4

Eczema

A resident at a skilled nursing facility presented with a severe case of eczema. The clinical manager and wound care nurse topically applied an ointment of the present invention. Within a few days, the eczema was barely visible.

Example 5

Incontinence Dermatitis

A resident at a skilled nursing facility presented with an ongoing case of incontinent dermatitis and denuded areas to the right posterior thigh. The clinical manager and wound care nurse topically applied an ointment of the present invention for one week. The affected areas were markedly improved and the wounds appeared to be healing faster.

Example 6

Mastectomy Wound

A patient presented with a mastectomy wound. An ointment of the present invention was topically applied. The wound healed.

Example 7

Pediatric Recurring Eczema

A 5 year old male patient presented with a severe case of recurring eczema. After trying other products without success, the caregiver topically applied the ointment of the present invention. After one night, the skin was dramatically improved. The cream seemed to sooth the affected skin.

Example 8

Pediatric Recurring Eczema

A 5 year old female patient presented with a severe case of recurring eczema. After trying other products without success, the caregiver topically applied the ointment of the present invention. After application, there was a tremendous difference in the skin—"it worked wonders". The product was also used on chaffed skin and successful results were obtained.

Example 9

Geriatric Eczema

A 73 year old male nursing home patient presented with a case of eczema to the chest and extremities. After trying multiple prescription creams and oral steroids without success, the caregiver topically applied the ointment of the present invention. After a few months, his skin was healed. There was no longer any red, scaling skin, nor any complaints of itching.

Example 10

Pediatric Foot Dermatitis

An 8 year old female patient presented with red, cracked, and fissured skin on the bottoms of her toes and feet. The condition had been ongoing for a few years. After trying antifungal products without success, the caregiver topically applied the ointment of the present invention every night. After one week, the cracks in the toes were healed and the feet look much better.

Example 11

Burn Wound

A 3rd grade teacher presented with a severe burn on her hand after an accident. After trying several other products without success, she topically applied the ointment of the present invention. Instantaneously upon application, the burning sensation was gone. The cream was applied daily and the hand was completely healed within three days and there was no scarring.

Example 12

Trauma Wound

A 6 year old boy fell off and was injured by a treadmill where the belt pulled the skin off his shoulder, resulting in a multiple damaged areas including a large approx. 3"×6" wound. The mother tried multiple first aid items with no success, and the boy started developing a fever and antibiotic creams were applied without success. Dressings were causing further damage to the skin. A composition of pH 9.2 was applied in 3 applications, 4 hours apart. The skin healed within one week from open wound to pink, regenerated skin.

Example 12

No Cleaning Required

In all clinical trials to date, the most commonly cited benefit among clinicians is that the composition does not have to be scraped off skin for bathing/cleaning

Example 13

Venous Stasis

Clinicians noted that in 10 days, legs improved in color/skin condition, and overall skin condition improved.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

We claim:

1. A permeable dermatological composition, comprising water and the following components in the following component weight ranges; petrolatum approximately 15% wt.; mineral oil approximately 8% wt.; ceresin wax approximately 5% wt.; dimethicone approximately 1% wt.; lanolin alcohol approximately 7% wt.; aluminum hydroxide approximately 0.75% wt.; magnesium hydroxide approximately 0.68% wt.; sorbitan sesquioleate less than 5% wt.; sorbitol less than 3% wt.; and preservatives less than 1% wt; and 0.1%-10% wt. of a litmus dye or other pharmaceutically acceptable acid-base indicator.

2. The composition according to claim 1, in the form of an ointment, lotion, cream, emulsion, suspension, ointment, gel, bath, soak, spray, powder, or foam.

3. The composition according to claim 1, in the form of a cream or an ointment.

4. The composition according to claim 1, in a delivery vehicle selected from a single use, individualized, sterile packets, a pre-soaked wrap, bandage or dressing, a pre-soaked undergarment, a pre-soaked wipe, treated applicator, an infused film for application to the skin, or an infused sponge with applicator stick for use in oral care to treat mouth sores.

5. The composition according to claim 1, in combination with an additional therapeutic agent.

* * * * *